United States Patent [19]

Grossman et al.

[11] Patent Number: 4,652,312
[45] Date of Patent: Mar. 24, 1987

[54] GLASS-CERAMIC COMPOSITIONS FOR DENTAL CONSTRUCTS

[75] Inventors: David G. Grossman, Corning; Janet L. M. Johnson, Painted Post, both of N.Y.

[73] Assignee: Corning Glass Works, Corning, N.Y.

[21] Appl. No.: 794,717

[22] Filed: Nov. 4, 1985

[51] Int. Cl.$^4$ .................. C09K 3/00; C03C 10/16
[52] U.S. Cl. ........................................ 106/35; 501/3
[58] Field of Search ............... 433/199; 106/35; 501/3

[56] References Cited

U.S. PATENT DOCUMENTS

| | | | |
|---|---|---|---|
| 2,920,971 | 1/1960 | Stookey | 501/38 |
| 3,486,872 | 12/1969 | Wojcik et al. | 501/57 |
| 3,839,055 | 10/1974 | Grossman | 501/3 |
| 3,840,394 | 10/1974 | Eppier | 428/446 |
| 4,414,281 | 11/1983 | Hoda | 428/433 |
| 4,431,420 | 2/1984 | Adair | 106/35 |
| 4,440,576 | 4/1984 | Flannery | 501/55 |
| 4,467,039 | 8/1984 | Beall et al. | 501/3 |
| 4,478,641 | 10/1984 | Adair et al. | 106/38.3 |

*Primary Examiner*—Theodore Morris
*Attorney, Agent, or Firm*—K. van der Sterre

[57] ABSTRACT

Tetrasilicic fluormica glass-ceramic compositions particularly suited for use in the preparation of dental restorations, consisting essentially in weight percent of about 45–70% $SiO_2$, 13–30% $MgO$, 5–20% $K_2O$, 0–2% $Al_2O_3$, 0–7% $ZrO_2$, 4–9% F and 1–4% BaO, and porcelain-glazed dental restorations prepared therefrom, are described.

5 Claims, 2 Drawing Figures

GLASS-CERAMIC COMPOSITIONS FOR DENTAL CONSTRUCTS

BACKGROUND OF THE INVENTION

1. Field of the Invention

The present invention relates generally to new compositions for glass-ceramic products and specifically to new glass-ceramic compositions particularly suited for the fabrication of dental constructs such as artificial teeth.

2. Description of the Prior Art

The use of glass-ceramic materials for the fabrication of dental constructs such as dental appliances, e.g., artificial denture plates, bridges and orthodontic brackets, and prosthetic devices such as inlays, onlays partial or full dentures, crowns, and other restorations has been described, for example, in U.S. Pat. No. 4,431,420. As noted in that patent, all such dental constructs should be (1) inert in the oral environment, (2) able to resist the forces of mastication, (3) capable of being shaped to a desired anatomical configuration, and (4) exhibit the aesthetic qualities of natural teeth.

Glass-ceramic materials offer unique advantages for dental applications of the kind described. Because such materials are supplied initially as glasses, they can be formed into desired product shapes by any of the various shaping techniques known to the glass technologist. Further, the glass shapes can be readily converted to highly crystalline bodies without change of shape by a suitable heat treatment, and thereafter exhibit the desirable physical and chemical characteristics of the predominant crystal phase developed on heating. Such properties may include very high abraded strength, chemical inertness, desirable thermal properties and good visual appearance.

U.S. Pat. No. 2,920,971 contains a general description of the basic principles of glass-ceramic technology and may be referred to for a further description of these materials. U.S. Pat. No. 3,839,055 describes a family of glass-ceramic materials identified as tetrasilicic fluormica glass-ceramics which are characterized by good strength and translucency and are therefore particularly well suited to the manufacture of dental constructs. European Patent EP No. 0083828 indicates a preferred range of tetrasilicic fluormica base compositions for dental applications. Those preferred base compositions, if defined according to current practice in weight percent on the oxide basis (except for fluorine which is reported on an elemental basis), consist essentially of about 45–70% $SiO_2$, 13–30% MgO, 5–20% $K_2O$, and 4–9% F. The addition of up to 2% $Al_2O_3$ and up to 7% $ZrO_2$ to these base compositions was found beneficial to stain resistance in the crystallized glass-ceramic material.

In forming dental constructs from glass-ceramic compositions such as above described, it is frequently desirable to apply to the construct, after thermal conversion to a tetrasilic fluormica body of the desired shape, a final outer layer in the form of an enamel or glaze. This outer layer (hereinafter 'glaze layer') which can be composed of sintered glass, porcelain or the like, can be helpful in controlling the final color and/or translucency of the construct without undesirably modifying its physical properties.

In attempting to develop procedures for applying porcelain glaze layers to portions of the exterior surfaces of dental constructs formed from certain tetrasilicic fluormica glass-ceramics (hereinafter sometimes 'mica glass-ceramics') difficulty had been encountered in consistently achieving a smooth, non-porous and defect-free glaze layer on the outer surface of those constructs formed from high-crystal-content glass-ceramic formulations. Frequently, what was instead achieved was a rough or porous surface film on the outer surface of the porcelain glaze. Further investigation revealed that the phenomenon of surface roughening was not limited to glazed constructs, but could be induced in unglazed bodies as well, simply by processing them through the standard glaze firing cycle. Obviously, surface porosity of any kind would be unacceptable in a dental construct for reasons of aesthetics and hygiene. A solution to the problem of poor glaze layer surface quality in glazed and unglazed mica glass-ceramic products was therefore needed.

SUMMARY OF THE INVENTION

The present invention provides improved compositions for mica glass-ceramics which can be employed to make glazed or unglazed glass-ceramic dental constructs of excellent surface quality. Compositions useful according to the invention are those consisting essentially, in weight percent on the oxide basis, of about 45–70% $SiO_2$, 13–30% MgO, 5–20% $K_2O$, 4–9% F, 0–2% $Al_2O_3$, 0–7% $ZrO_2$, and 1–4% BaO. These compositions, when converted to mica glass-ceramics by conventional heat treatment, provide unglazed constructs exhibiting chemical and physical properties essentially equivalent to prior art glass-ceramics of the same type. In addition, however, the resulting glass-ceramics exhibit improved stability against surface disruption during post-crystallization firing treatments, and thus have improved utility for use both as a substrate for fired porcelain or other glaze layers, and as an unglazed body. Thus the appearance of porosity in fired glaze layers and in unglazed products made from the above-described compositions is significantly reduced or avoided.

Utilizing the above compositions, then, the invention provides dental constructs comprising a body portion consisting of a tetrasilicic fluormica glass-ceramic having the composition above described and, optionally and preferably, a non-porous glaze layer covering at least a portion of the surface of the body portion. Such constructs can be manufactured with improved efficiency due to the greatly reduced incidence of porosity-related enameling defects in the glazed products.

DESCRIPTION OF THE DRAWING

The invention may be further understood by reference to the drawing, wherein.

DETAILED DESCRIPTION

The steps of forming a dental construct such as an artificial tooth section from a tetrasilicic fluormica glass-ceramic typically comprise: (1) forming from the mouth of the patient an accurate impression of the oral bonding surface to which the artificial tooth section is to be bonded, and preparing therefrom a master model accurately reflecting the bonding surface, (2) preparing on the model a wax or other pattern of the required tooth section or other construct, and thereafter separating the pattern from the model, (3) forming a casting mold around the wax pattern and then removing the wax, and (4) casting glass for the artificial tooth section into the casting mold.

After the glass artificial tooth section is thus prepared, it is heat-treated to convert it to a mica glass-ceramic material. This may be done in a refractory embedment (such as described in U.S. Pat. No. 4,478,641) in order to prevent distortion of the glass section during heat treatment, although an embedment is not required in every case. Thereafter, if a glaze is to be applied to selected surface portions of the glass-ceramic tooth section, the thin skin layer of the section in contact with the embodiment material, which does not crystallize to mica, is customarily removed. The porcelain or other enamel slip is then applied and the tooth section is fired to form the final glaze layer.

In investigating the cause of surface porosity in dental restorations produced as above described, we have observed that the porous surface does not appear on unglazed surfaces of the construct until after the material has been processed through a porcelain firing cycle. We now believe that the primary cause of this surface effect is moisture adsorbed by the tetrasilicic fluormica material, a phenomenon which can occur relatively rapidly after the removal of the surface material from the glass-ceramic for subsequent enameling and porcelain firing. Apparently, this moisture is violently driven off during porcelain firing and disrupts the surface and any overlying glaze.

Figure 1:
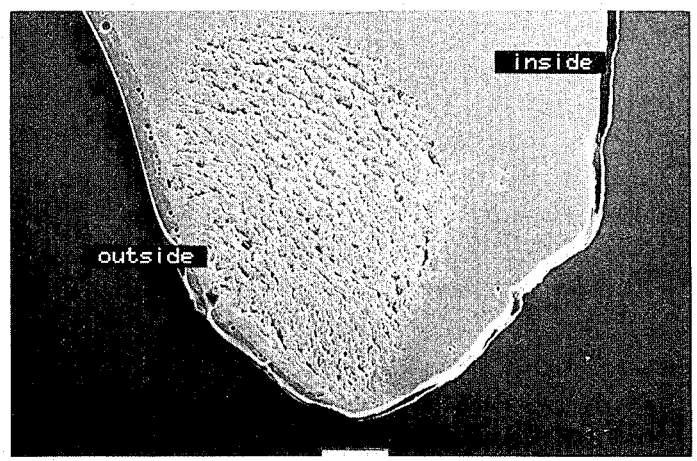
FIG. 1 is an electron photomicrograph of a cross-section of a prior art mica glass-ceramic article exhibiting firing-induced porosity.

FIG. 1 of the drawing is an electron photomicrograph of an etched cross-section of a glazed glass-ceramic dental crown taken near the margin or thin edge section of the crown. The white bar on the lower margin of the micrograph represents a dimension of 100 microns.

The crown shown in FIG. 1 was formed of a high-crystallinity prior art tetrasilicic fluormica glass-ceramic composition free of added BaO, and was processed through a conventional porcelain glazing cycle. The large, generally circular region of porosity appearing within the lower outside section of the crown margin is due, we believe, to moisture adsorbed by the mica material during a stnadardized hydration testing treatment after removal of surface skin material therefrom.

While it is possible to avoid the water adsorption problem, e.g., by porcelain-glazing the construct immediately after removal of any surface material therefrom and/or by using mild porcelain firing treatments, such measures add undesirable constraints to the fabrication process, requiring special attention by the fabricating dental technician. Accordingly, a solution which would not further complicate the fabrication procedure is needed.

According to the present invention, mica glass-ceramic compositions of conventional composition are modified by the addition of controlled amounts of BaO thereto, which additions have been found to reduce or eliminate surface disruption and porosity formation during procelain firing. Apparently, such BaO additions reduce the extent of water adsorption by the glass-ceramic material, yet do not adversely affect the strength, chemical durability, or essential translucency of the material.

Figure 2:
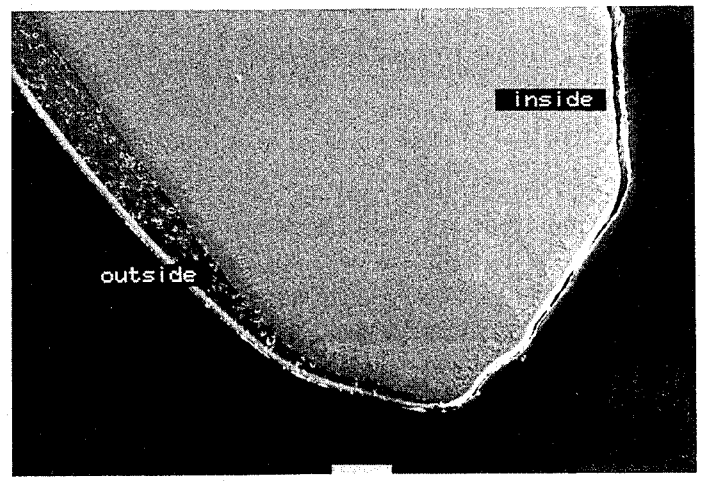
FIG. 2 is an electron photomicrograph of a cross-section of a mica glass-ceramic article provided according to the invention exhibiting reduced firing-induced porosity.

FIG. 2 of the drawing is an electron photomicrograph of an etched cross-section of a second glazed glass-ceramic dental crown taken near the crown margin, the white bar on the lower margin of the micrograph representing a dimension of 100 microns. The crown shown in FIG. 2 was formed of a tetrasilicic fluormica glass-ceramic according to the invention, containing about 1.9% of BaO by weight, and was also processed through a conventional glazing cycle. While this crown underwent a standardized hydration test treatment after surface skin removal in the same manner as the crown shown in FIG. 1, it exhibited substantial freedom from porosity due to hydration or other cause. We attribute this result to the beneficial effect of the BaO constituent on the hydration stability of the material.

Compositions which are particularly preferred for use according to the invention are those consisting essentially, in weight percent on the oxide basis, of about 55–65% $SiO_2$, 14–19% $MgO$, 8–18% $K_2O$, 0.05–2% $Al_2O_3$, 0.5–7% $ZrO_2$, 4–9% F, and 1–4% BaO. The amount of BaO employed has a significant effect on the results. If less than the specified amount of BaO is included, water adsorption by the glass-ceramic material is sufficiently rapid that surface porosity formation in the glaze may still be a problem. On the other hand, the use of more than the specified amount of BaO can adversely affect the translucency of the material.

While porcelain is the glaze most commonly employed for the fabrication of dental constructs (techniques for applying these glazes and tinting them to match existing tooth color being well developed), other enameling materials including clear glass enamels or the like may alternatively be employed to form the glaze layer. The glass-ceramic compositions of the invention may be advantageously employed with any of the various enameling compositions useful in the production of glaze layers on dental constructs, since all of these compositions would be expected to be adversely affected to some degree by the release of adsorbed moisture from the underlying material during glaze firing.

The invention may be further understood by reference to the following illustrative example.

EXAMPLE I

Two glass melts suitable for preparing mica glass-ceramics are formulated. These melts, identified as Melt A, a conventional composition, and Melt B, a composition according to the present invention, have the following compositions, in parts by weight:

| Melt A | Melt B |
|---|---|
| $SiO_2$: 62.2 | $SiO_2$: 62.2 |
| MgO: 16.2 | MgO: 16.2 |
| $K_2O$: 12.6 | $K_2O$: 11.6 |
| $ZrO_2$: 4.76 | $ZrO_2$: 4.76 |
| F: 5.55 | F: 5.55 |
| $Al_2O_3$: 0.48 | $Al_2O_3$: 0.48 |
|  | BaO: 1.7 |

Small glass sample pieces the size of a small dental construct are cast from these melts, and the glass pieces are subjected to crystallization heat treatments to convert them to mica glass-ceramic pieces, thereafter identified as Samples A and B, respectively. Crystallization is accomplished by heating the samples at a rate of about 200° C. per hour to 1075° C., holding at that temperature for 6 hours, and thereafter slowly cooling to room temperature. In both cases, heat treatment is carried out while the samples are embedded in an investment consisting of 15% plaster of Paris and 85% leucite, as described in U.S. Pat. No. 4,478,641.

Mica glass-ceramic Samples A and B produced by the above process are subjected to a standardized moisture test, referred to as a hydration test, wherein the glazing characteristics of each sample after forced hydration are evaluated. Each sample is first abraded to remove approximately 45 microns of non-micaceous surface material; soaked in water at 95° C. for 24 hours; removed, and dried. Each sample is then covered with a porcelain slurry to form a surface coating; dried; and finally fired at 1750° F. for three minutes to mature the surface coating to a glaze layer.

Examination of Sample A (the prior art composition) following the above test reveals a heavy porous surface film on the fired porcelain glaze layer. In contrast, Sample B (the mica glass-ceramic provided according to the invention) exhibits a smooth, defect-free porcelain glaze layer over the entire glazed surface of the sample.

EXAMPLE II

Optional constituents, in addition to $Al_2O_3$ and $ZrO_2$, may be included in the glass-ceramic compositions of the invention without loss of the required enameling characteristics. An example of a permissible optional constituent is SrO, in an amount ranging up to about 5% by weight of the composition.

Table I below reports the glazing characteristics exhibited by porcelain-glazed mica glass-ceramics containing varying amounts of SrO. Small glass samples as in Example I were in each case converted to glazed crystalline mica glass-ceramics utilizing the heat treatment and glazing procedures of Example I, and the hydration test used in Example I was used to evaluate the glazing characteristics of the samples. Table I includes, in addition to the body composition of each glazed sample (in parts by weight), the amount of surface porosity, if any, appearing on the surface of each sample after hydration testing.

TABLE I

| Sample I.D. | C | D | E |
|---|---|---|---|
| Composition: | | | |
| $SiO_2$ | 62.2 | 62.2 | 62.2 |
| MgO | 16.2 | 16.2 | 16.2 |
| $K_2O$ | 9.9 | 8.4 | 9.8 |
| $ZrO_2$ | 4.76 | 4.76 | 4.76 |
| $Al_2O_3$ | 0.48 | 0.48 | 0.48 |
| BaO | 1.8 | 1.8 | 2.0 |
| F | 5.55 | 5.55 | 5.55 |
| SrO | 1.5 | 3.0 | 1.5 |
| Surface Porosity: | None | None | None |

Of course, the foregoing examples are merely illustrative of glass-ceramic compositions which could be utilized to form glazed dental constructs in accordance with the invention, and it will be apparent that numerous variations and modifications of the particular embodiments described herein may be adopted in the practice of the invention within the scope of the appended claims.

We claim:
1. A tetrasilic fluormica glass-ceramic article having a composition consisting essentially, in weight percent on the oxide basis, of about 45–70% $SiO_2$, 13–30% MgO, 5–20% $K_2O$, 4–9% F, 0–2% $Al_2O_3$, 0–7% $ZrO_2$, and 1–4% BaO.
2. An article in accordance with claim 1 which is in the form of a dental construct.
3. A dental construct comprising a tetrasilicic fluormica glass-ceramic body portion and a glaze layer covering at least part of the surface of the body portion, wherein the tetrasilicic fluormica body portion has a composition consisting essentially, in weight percent on the oxide basis, of about 45–70% $SiO_2$, 13–30% MgO, 5–20% $K_2O$, 4–9% F, 0–2% $Al_2O_3$, 0–7% $ZrO_2$, and 1–4% BaO.
4. A dental construct in accordance with claim 3 wherein the glaze layer consists of a porcelain glaze.
5. A dental construct in accordance with claim 4 wherein the tetrasilicic fluormica body portion consists essentially, in weight percent on the oxide basis, of about 55–65% $SiO_2$, 14–19% MgO, 8–18% $K_2O$, 0.05–2% $Al_2O_3$, 0.5–7% $ZrO_2$, 4–9% F and 1–4% BaO.

* * * * *